United States Patent
Sims

(10) Patent No.: US 9,943,661 B2
(45) Date of Patent: Apr. 17, 2018

(54) DUAL EXPANSION CHAMBER WITH INTERNAL CONNECTING TUBE FOR USE WITH AN OXYGEN CONCENTRATOR

(71) Applicant: Chart Inc., Ball Ground, GA (US)

(72) Inventor: Matthew Sims, Ball Ground, GA (US)

(73) Assignee: Chart Inc., Ball Ground, GA (US)

( * ) Notice: Subject to any disclaimer, the term of this patent is extended or adjusted under 35 U.S.C. 154(b) by 601 days.

(21) Appl. No.: 14/548,746

(22) Filed: Nov. 20, 2014

(65) Prior Publication Data

US 2015/0136126 A1    May 21, 2015

Related U.S. Application Data

(60) Provisional application No. 61/906,624, filed on Nov. 20, 2013.

(51) Int. Cl.
*A61M 16/08* (2006.01)
*A61M 16/10* (2006.01)

(52) U.S. Cl.
CPC .... *A61M 16/0875* (2013.01); *A61M 16/0866* (2014.02); *A61M 16/101* (2014.02); *A61M 16/105* (2013.01); *A61M 16/0816* (2013.01); *A61M 2202/0208* (2013.01); *A61M 2205/42* (2013.01); *A61M 2205/75* (2013.01)

(58) Field of Classification Search
CPC .......... A61M 16/0875; A61M 16/0866; A61M 16/101; A61M 16/105; A61M 16/0816; A61M 2202/0208; A61M 2205/42; A61M 2205/75

USPC ........ 181/212, 247, 249, 252, 256, 264, 269
See application file for complete search history.

(56) References Cited

U.S. PATENT DOCUMENTS

| | | | | |
|---|---|---|---|---|
| 4,111,278 A * | 9/1978 | Bergman | ................ | F01N 1/089 181/249 |
| 4,589,516 A * | 5/1986 | Inoue | ........................ | F01N 1/10 181/256 |
| 5,196,654 A * | 3/1993 | DiFlora | .................. | F01N 1/083 181/229 |
| 5,208,429 A * | 5/1993 | Field | .................. | F02M 35/1222 181/229 |
| 5,285,026 A * | 2/1994 | Lemetyinen | ............ | F24F 13/24 181/224 |
| 6,530,452 B1 * | 3/2003 | Pettersson | ................. | D21F 1/48 181/224 |
| 6,702,880 B2 * | 3/2004 | Roberts | .............. | B01D 46/0023 181/231 |
| 7,141,101 B2 * | 11/2006 | Amann | .............. | B01D 46/0023 181/229 |
| 7,153,107 B1 * | 12/2006 | Maddox, Jr. | ........ | F04B 39/0055 181/281 |

(Continued)

FOREIGN PATENT DOCUMENTS

JP      10245203 A *   9/1998   .............. F16L 55/02
JP   2001120662 A *   5/2001

*Primary Examiner* — Jeremy Luks
(74) *Attorney, Agent, or Firm* — Cook Alex Ltd.; R. Blake Johnston

(57) ABSTRACT

A device combines a muffler and a filter such as for use with an air compressor. The device utilizes dual expansion chambers with an internal connecting tube to filter the air entering an air intake port of an air compressor or oxygen concentrator. The device attenuates sound that emanates from airflow through the chambers.

8 Claims, 6 Drawing Sheets

(56) References Cited

U.S. PATENT DOCUMENTS

| | | | |
|---|---|---|---|
| 8,011,470 B2 * | 9/2011 | Gurnee | A61G 10/026 |
| | | | 181/229 |
| 8,196,702 B2 * | 6/2012 | Park | F01N 1/04 |
| | | | 181/239 |
| 2003/0172931 A1 | 9/2003 | Kerechanin et al. | |
| 2004/0000310 A1 | 1/2004 | Wickham et al. | |
| 2008/0245605 A1 * | 10/2008 | Maeda | F01N 1/084 |
| | | | 181/254 |
| 2009/0025564 A1 | 1/2009 | Kuwabara | |
| 2012/0055340 A1 | 3/2012 | Wilkinson et al. | |
| 2015/0059741 A1 * | 3/2015 | Ota | A61M 16/10 |
| | | | 128/202.26 |

* cited by examiner

DUAL EXPANSION CHAMBER WITH INTERNAL CONNECTING TUBE FOR USE WITH AN OXYGEN CONCENTRATOR

REFERENCE TO PRIORITY DOCUMENT

This application claims priority to U.S. Provisional Patent Application Ser. No. 61/906,624, entitled "DUAL EXPANSION CHAMBER WITH INTERNAL CONNECTING TUBE FOR USE WITH AN OXYGEN CONCENTRATOR" and filed on Nov. 20, 2013. Priority to the aforementioned filing date is claimed and the provisional patent application is incorporated herein by reference.

BACKGROUND

An oxygen concentrator is a device that is used by a patient to treat conditions such as emphysema and chronic obstructive pulmonary disease (COPD). The concentrated oxygen or O2 helps oxygen patients receive the level of oxygen their body needs. Such oxygen concentrators are often used in a home environment or other environment, such as a nursing home, where loud noises can be undesirable.

The loud noise generation in the patient environment of an oxygen concentrator is downside as it can annoy or distract the patient or others in the environment. A typical oxygen concentrator includes an air compressor, which generates a loud noise as it intakes air and this typically constitutes a great amount of the unit noise level. The air compressor uses a single air expansion chamber that often does not provide sufficient noise suppression.

In view of the foregoing, there is a need for improved devices that are configured to muffle air that enters an air compressor such as for use in medical environments.

SUMMARY

Disclosed is a device that combines a muffler and a filter such as for use with an air compressor. The device utilizes dual expansion chambers with an internal connecting tube to filter the air entering an air intake port of an air compressor or oxygen concentrator. The device attenuates sound that emanates from airflow through the chambers. The device is described in an example context of being used with an oxygen concentrator although it should be appreciated that the device can be used with any compressor or pump for attenuating noise and/or filtering air.

In one aspect, there is disclosed an air expansion chamber device for an airflow device, comprising: a housing having an inlet and an outlet; a first chamber inside the housing, wherein the inlet communicates with the first chamber; a second chamber inside the housing, wherein the second chamber communicates with the outlet; and a connecting tube contained entirely within the housing, wherein the connecting tube defines an internal lumen that provides a passage for air to flow from the first chamber to the second chamber, and wherein the connecting tube has a length that is equal to the length of at least one of the chambers in a direction along the longitudinal axis of the connecting tube.

The details of one or more variations of the subject matter described herein are set forth in the accompanying drawings and the description below. Other features and advantages of the subject matter described herein will be apparent from the description, the drawings, and the claims.

DETAILED DESCRIPTION

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Disclosed is a device that combines a muffler and a filter for use with an air compressor. The device utilizes dual expansion chambers with an internal connecting tube to filter the air entering an intake port of an air compressor or oxygen concentrator. The device attenuates sound that emanates from airflow through the chambers.

Although the device is described herein as being used for an oxygen concentrator, it may be used with any system utilizing an air compressor, pump, or black box producing intake or exhaust gas flow. The device may be particularly useful for air compressors or other devices of a cyclical/pulsating nature. The device has particularly advantageous use for applications where low flow restriction and broadband noise attenuation (especially in the mid to high frequencies) is desired. The device when acting as a muffler does not necessarily need to be used with a filtering function.

Figure 1:
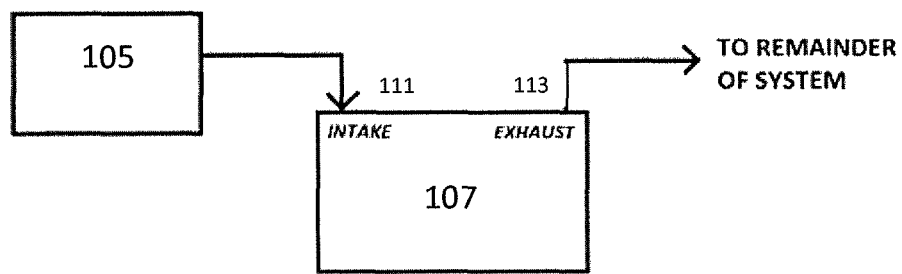
FIG. 1 shows a schematic representation of a muffler and/or filter system coupled to a compressor.

FIG. 1 shows a schematic view of a system including an airflow chamber device 105 through which a gas flows into a compressor 107 (or pump.) The gas enters the device 105, flows into an intake inlet 111 of the compressor 107, and then flows out of an exhaust 113 of the compressor 107 toward a system. From the exhaust, the gas may flow and be used in a system such as an oxygen concentrator.

Figure 2A:
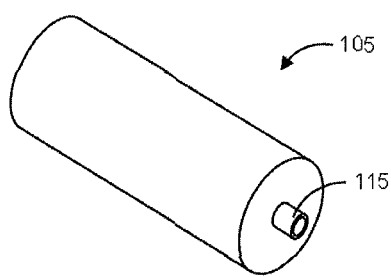
FIG. 2A shows a perspective, schematic view of a dual expansion airflow chamber for use with an air compressor of an oxygen concentrator.
Figure 2B:
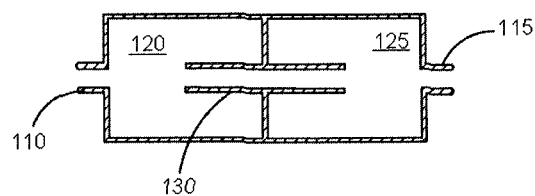
FIG. 2B shows a side, cross-sectional view of the chamber.

FIG. 2A shows an external view of an example of the airflow chamber device 105. FIG. 2B shows a cross-sectional view of the device 105. The embodiments of FIGS. 2A and 2B are for example only. It should be appreciated that the device 105 can vary in size and shape. The device 105 includes an inlet 110 through which air can flow into the device and an outlet 115 through which air can exit the device. An internal portion of the device 105 defines a dual chamber configuration including a first chamber 120 and a second chamber 125, each configured to contain a gas or support a flow of gas therethrough. An internal connecting tube 130 has a lumen that provides airflow communication between the first chamber 120 and the second chamber 125 such that gas can flow into the first chamber 120 via the inlet 110, flow into the second chamber 125 via the connecting tube 130, and flow out of the second chamber 125 via the outlet 15 toward the compressor 107. The internal connecting tube 130 fluidly connects the two chambers in series. In another embodiment, the device includes more than two chambers connected in series by multiple connecting tubes.

Figure 3A:
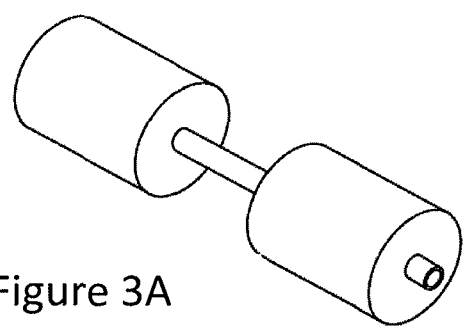
FIGS. 3A and 3B show perspective and side views of dual expansion airflow chambers with a connecting tube positioned external to chambers.
Figure 3B:
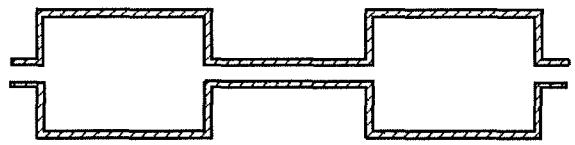

As best shown in FIG. 2B, the chambers are positioned in series relative to airflow through the device 105 and the connecting tube 130 is internal to the two chambers. That is, the connecting tube 130 is contained entirely within the first and second chambers such that a portion of the connecting tube 130 is contained within the first chamber 120 and a portion of the connecting tube 130 is also contained in the second chamber 125. The embodiment of FIGS. 2A and 2B differs from an embodiment wherein a connecting tube that is external to the chambers, such as shown in FIGS. 3A and 3B.

It has been shown that increased noise attenuation can be gained by utilizing an internal connecting tube where the connecting tube 130 is entirely internal to the chambers as shown in FIGS. 2A and 2B. Moreover, this construction yields additional benefits in that overall muffler size envelope is reduced with respect to what is shown in FIGS. 3A and 3B. The use of two or more chambers increases the effectiveness of the noise attenuation for a muffler with respect to the use of only a single chamber as it simulates multiple mufflers in series, where each further chamber attenuates the magnitude of its respective input noise level. In addition, a connecting tube approximately the same physical length as the chambers themselves eliminates a noise pass region in the attenuation versus noise frequency response spectrum.

Figure 4:
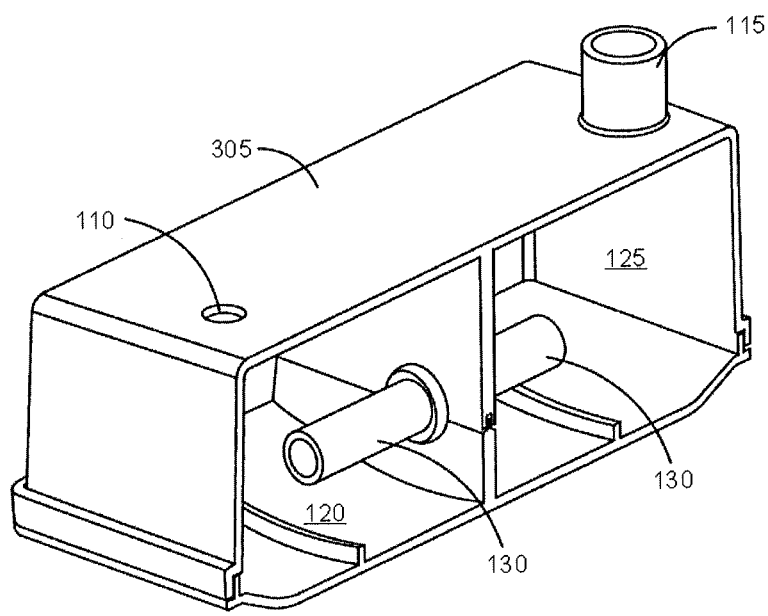
FIG. 4 shows a perspective view of an embodiment of the dual expansion chamber muffler device.

The size and shape of the connecting tube 130 can vary. In the embodiment of FIG. 4, the connecting tube 130 is cylindrical although this can vary. For example, the connecting tube may be non-circular in cross-section or can be non-straight. In an embodiment, the connecting tube 130 has a length that is equal or about equal to the length of one of the chambers in a direction along the longitudinal axis of the connecting tube 130. For example, the connecting tube may have a length of X. In an embodiment, the length of the first chamber and the second chamber are each equal to the length X of the connecting tube. The first chamber and the second chamber desirably have equal lengths with that length also being equal to the length of the connecting tube. The maximum height of the first and second chambers is preferably high with a larger height being preferred.

FIG. 4 shows a perspective view of an embodiment of the dual expansion chamber muffler device 105. The device is shown in cross-section to show the internal chambers. It should be appreciated that the chambers in the actual device are enclosed by outer walls with an inlet 110 and an outlet 115 providing airflow entry and exit pathways for air to flow through the chambers. The device 105 has an outer housing 305 that defines the chambers 120 and 125 with an internal wall dividing the chambers. The chambers can vary in size and shape. The connecting tube 130 is positioned so that it extends through the dividing wall with the tube forming a lumen that permits air to flow from the first chamber 120 to the second chamber 125. An intake port 110 is flush with a top surface of the housing 305 and an outlet port 115 is formed of a tube that protrudes from the housing. The size, shape, and positions of the inlet and outlet ports may vary.

Figure 5:
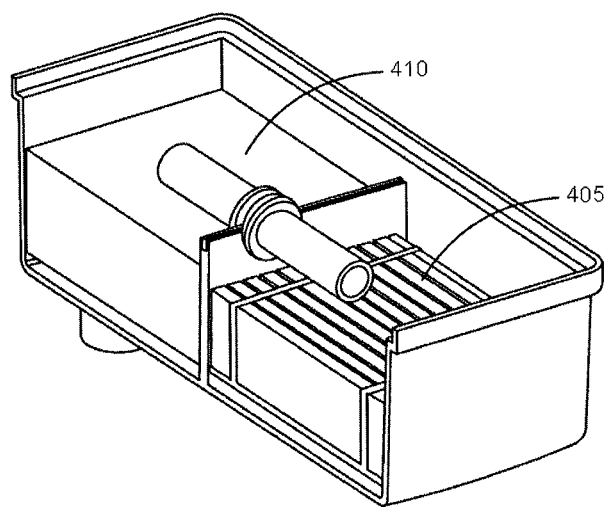
FIG. 5 shows an embodiment of the device that includes a muffling element in the second chamber and a filter element in the first chamber.
Figure 6:
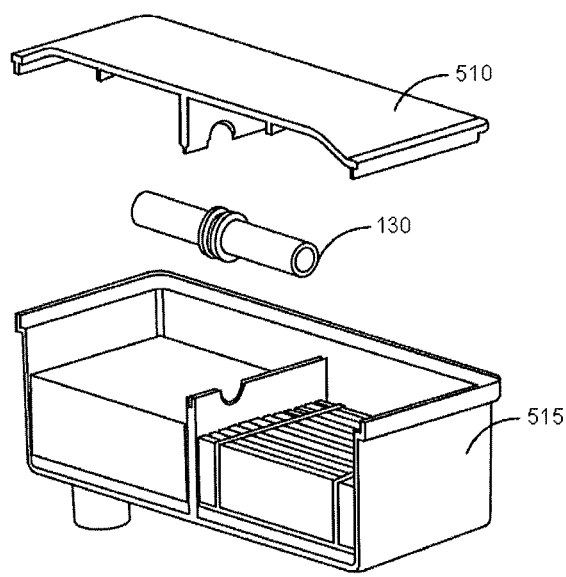
FIG. 6 shows an exploded view of an embodiment of the device.

FIG. 5 shows an embodiment of the device 105 that includes a muffling element 410 in the second chamber and a filter element 405 in the first chamber. The muffling element is made of a material or is otherwise configured such that it muffles noise from fluid passing therethrough. The muffling element may vary in material and it can be, for example, a piece of reticulated foam. It should be appreciated that the size and relative positions of these elements may vary. In an embodiment, the filter element 405 is made of pleated borosilicate microfiber paper although the material may vary. The device in FIGS. 5 and 6 is shown in partial cross-section to show the internal chambers. It should be appreciated that the chambers in the actual device are enclosed by outer walls with an inlet and an outlet providing airflow entry and exit pathways for air to flow through the chambers.

With reference to the exploded view of FIG. 6, the housing may be formed of a base member 515 that attaches to a cover member 510. The cover member may attach to the base member in a variety of manners, such as in a tongue and groove arrangement. The connecting tube 130 may be secured in place between the base member and the cover member in the assembled device.

In an embodiment, the housing is 4 inches long, the connecting tube has a 0.25" diameter and the chambers are about 1.75 inches in diameter or width.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. An air expansion chamber device for an airflow device, comprising:
    a housing having an inlet and an outlet pipe that extends along a first axis;
    a first chamber inside the housing, wherein the inlet communicates with the first chamber;
    a second chamber inside the housing, wherein the second chamber communicates with the outlet;
    a connecting tube contained entirely within the housing, wherein the connecting tube defines an internal lumen that provides a passage for air to flow from the first chamber to the second chamber, and wherein the connecting tube has a length that is equal to the length of at least one of the chambers in a direction along the longitudinal axis of the connecting tube, wherein the connecting tube has a first portion cantilevered into the first chamber and a second portion cantilevered into the second chamber, and wherein the first axis of the outlet pipe is transverse to the longitudinal axis of the connecting tube;
    a filter element in the first chamber, wherein the filter element covers an entryway into the outlet pipe
    a muffler element in the second chamber, wherein the filter element covers the inlet.

2. A device as in claim 1, wherein the air expansion chamber device is connected to a compressor.

3. A device as in claim 1, wherein the air expansion chamber device is connected to an oxygen concentrator.

4. A device as in claim 1, wherein the housing includes a removable cover.

5. A device as in claim 1, wherein connecting tube is positioned at least partially in the first chamber or second chamber.

6. A device as in claim 1, wherein the connecting tube has a cylindrical outer surface.

7. A device as in claim 1, further comprising a single wall separating the first chamber from the second chamber.

8. A device as in claim 1, wherein the connecting tube has a length of X and wherein each of the first and second chambers also have a length of X.

* * * * *